United States Patent
Soble et al.

(10) Patent No.: US 6,997,867 B2
(45) Date of Patent: Feb. 14, 2006

(54) FLEXIBLE SLEEVE SLIDINGLY TRANSFORMABLE INTO A LARGE SUCTION SLEEVE

(75) Inventors: Jon Soble, Evanston, IL (US); Anthony Tremaglio, Hopkington, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/389,306

(22) Filed: Mar. 14, 2003

(65) Prior Publication Data

US 2003/0176769 A1 Sep. 18, 2003

Related U.S. Application Data

(63) Continuation of application No. 09/579,995, filed on May 26, 2000, now Pat. No. 6,547,724.
(60) Provisional application No. 60/136,007, filed on May 26, 1999.

(51) Int. Cl.
*A61B 1/00* (2006.01)

(52) U.S. Cl. ..................... 600/121; 600/156; 600/153
(58) Field of Classification Search ............... 600/156, 600/154, 153, 157, 114, 121; 606/115
See application file for complete search history.

(56) References Cited

U.S. PATENT DOCUMENTS 4,146,019 A      3/1979   Bass et al. ................... 128/6
4,445,892 A      5/1984   Hussein et al. ............. 604/101
4,538,594 A      9/1985   Boebel et al.
4,569,344 A      2/1986   Palmer ................. 128/207.16
4,784,117 A     11/1988   Miyazaki
5,287,845 A      2/1994   Faul et al.
5,347,992 A      9/1994   Pearlman et al. ............. 128/4

(Continued)

FOREIGN PATENT DOCUMENTS

| DE | 42 36 329 A1 | 5/1994 |
| DE | 296 18 589 U1 | 3/1997 |
| DE | 196 03 198 A1 | 7/1997 |
| EP | 0 352 984 A1 | 1/1990 |
| EP | 0 531 822 A1 | 3/1993 |
| WO | WO 94/06506 | 3/1994 |
| WO | WO 97/36536 | 10/1997 |

OTHER PUBLICATIONS

Grasso, III, M.D. "Chapter 32—Flexible Fiberoptic Ureteropyleoscopy," *Smith's Textbook of Endourology*, vol. 1, 1996, Quality Medical Publishing Inc., pp. 443–454.

*Primary Examiner*—Beverly M. Flanagan

(57) ABSTRACT

A sleeve is provided for placing over a flexible endoscope. The sleeve has a port between its distal and proximal openings and the port is connected to a vacuum source. Once the endoscope is retracted proximal to the suction port, the sleeve's proximal opening is sealed off and the entire sleeve is turned into a suction lumen. Devices and methods in accordance with the invention provide improvement in removing materials from body cavities, especially in removing stones from the upper urinary tract.

29 Claims, 4 Drawing Sheets

U.S. PATENT DOCUMENTS

| | | | | |
|---|---|---|---|---|
| 5,349,950 | A | 9/1994 | Ulrich et al. | 128/207.16 |
| 5,363,860 | A | 11/1994 | Nakao et al. | 128/760 |
| 5,368,017 | A | 11/1994 | Sorenson et al. | 128/200.26 |
| 5,368,560 | A | 11/1994 | Rambo et al. | 604/35 |
| D353,886 | S | 12/1994 | Bales et al. | D24/108 |
| 5,415,157 | A | 5/1995 | Welcome | |
| 5,419,769 | A | 5/1995 | Devlin et al. | 604/119 |
| 5,421,346 | A | 6/1995 | Sanyal | 128/750 |
| 5,427,144 | A | 6/1995 | Teets et al. | 137/614.2 |
| 5,429,596 | A | 7/1995 | Arias et al. | 604/21 |
| 5,429,619 | A | 7/1995 | Furnish | 604/283 |
| 5,447,494 | A | 9/1995 | Dorsey, III | 604/43 |
| 5,449,145 | A | 9/1995 | Wortrich | 251/322 |
| 5,449,357 | A | 9/1995 | Zinnanti | 606/49 |
| 5,451,216 | A | 9/1995 | Quinn | 604/270 |
| 5,453,088 | A | 9/1995 | Boudewijn et al. | 604/43 |
| 5,460,613 | A | 10/1995 | Ulrich et al. | 604/118 |
| 5,462,529 | A | 10/1995 | Simpson et al. | 604/101 |
| 5,476,450 | A | 12/1995 | Ruggio | 604/93 |
| 5,486,161 | A | 1/1996 | Lax et al. | 604/22 |
| 5,490,503 | A | 2/1996 | Hollister | 128/205.12 |
| 5,496,268 | A | 3/1996 | Perla | 604/27 |
| 5,496,287 | A | 3/1996 | Jinotti | 604/249 |
| 5,496,314 | A | 3/1996 | Eggers | 606/41 |
| 5,503,616 | A | 4/1996 | Jones | 600/155 |
| 5,507,797 | A | 4/1996 | Suzuki et al. | 606/140 |
| 5,513,628 | A | 5/1996 | Coles et al. | 128/200.26 |
| 5,520,175 | A | 5/1996 | Fry | 128/207.15 |
| 5,527,292 | A | 6/1996 | Adams et al. | 604/171 |
| 5,536,234 | A | 7/1996 | Newman | 600/104 |
| 5,551,448 | A | 9/1996 | Matula et al. | 128/897 |
| 5,554,136 | A | 9/1996 | Luther | 604/264 |
| 5,556,367 | A | 9/1996 | Yabe et al. | |
| 5,562,640 | A | 10/1996 | McCabe et al. | 604/280 |
| 5,569,204 | A | 10/1996 | Cramer | 604/164 |
| 5,569,219 | A | 10/1996 | Hakki et al. | 604/282 |
| 5,571,088 | A | 11/1996 | Lennox et al. | 604/96 |
| 5,573,504 | A | 11/1996 | Dorsey, III | 604/35 |
| 5,575,753 | A | 11/1996 | Yabe et al. | 600/123 |
| 5,575,756 | A | 11/1996 | Karasawa et al. | |
| 5,575,772 | A | 11/1996 | Lennox | 604/96 |
| 5,579,762 | A | 12/1996 | Lee | 128/207.14 |
| 5,582,161 | A | 12/1996 | Kee | 128/200.26 |
| 5,582,166 | A | 12/1996 | Lee | 128/207.14 |
| 5,582,167 | A | 12/1996 | Joseph | 128/207.15 |
| 5,595,172 | A | 1/1997 | Reese | 128/200.26 |
| 5,598,840 | A | 2/1997 | Iund et al. | 128/207.14 |
| 5,603,703 | A | 2/1997 | Elsberry et al. | 604/268 |
| 5,605,537 | A | 2/1997 | Ivey | 604/21 |
| 5,611,336 | A | 3/1997 | Page et al. | 128/207.16 |
| 5,626,560 | A | 5/1997 | Söring | 604/22 |
| 5,637,075 | A | 6/1997 | Kikawada | 600/153 |
| 5,642,726 | A | 7/1997 | Owens et al. | 128/200.26 |
| 5,643,174 | A | 7/1997 | Yamamoto et al. | 600/114 |
| 5,645,048 | A | 7/1997 | Brodsky et al. | 128/202.27 |
| 5,653,231 | A | 8/1997 | Bell | 128/207.16 |
| 5,664,564 | A | 9/1997 | Palmer | 128/205.19 |
| 5,667,475 | A | 9/1997 | Laser et al. | 600/127 |
| 5,676,136 | A | 10/1997 | Russo | 128/205.24 |
| 5,681,262 | A | * | 10/1997 | Isse | 600/127 |
| 5,681,336 | A | 10/1997 | Clement et al. | 606/159 |
| 5,688,222 | A | 11/1997 | Hluchy et al. | |
| 5,697,888 | A | 12/1997 | Kobayashi et al. | |
| 5,713,849 | A | 2/1998 | Bosma et al. | 604/28 |
| 5,718,709 | A | 2/1998 | Considine et al. | 606/115 |
| 5,725,478 | A | 3/1998 | Saad | 600/157 |
| 5,728,129 | A | 3/1998 | Summers | 606/170 |
| 5,730,727 | A | 3/1998 | Russo | 604/118 |
| 5,733,298 | A | 3/1998 | Berman et al. | 606/167 |
| 5,749,858 | A | 5/1998 | Cramer | 604/164 |
| 5,775,325 | A | 7/1998 | Russo | 128/205.12 |
| 5,779,624 | A | * | 7/1998 | Chang | 600/114 |
| 5,779,687 | A | 7/1998 | Bell et al. | 604/265 |
| 5,791,337 | A | 8/1998 | Coles et al. | 128/200.26 |
| 5,807,311 | A | 9/1998 | Palestrant | 604/28 |
| 5,823,940 | A | 10/1998 | Newman | 600/105 |
| 5,827,229 | A | 10/1998 | Auth et al. | 604/171 |
| 5,827,243 | A | 10/1998 | Palestrant | 604/282 |
| 5,836,918 | A | 11/1998 | Dondlinger | 604/171 |
| 5,840,015 | A | 11/1998 | Ogino | 600/159 |
| 5,843,022 | A | 12/1998 | Willard et al. | |
| 5,855,549 | A | 1/1999 | Newman | 600/135 |
| 5,863,287 | A | 1/1999 | Segawa | |
| 5,871,441 | A | 2/1999 | Ishiguro et al. | 600/133 |
| 5,882,348 | A | 3/1999 | Winterton et al. | 604/283 |
| 5,919,174 | A | 7/1999 | Hanson | 604/283 |
| 5,931,831 | A | 8/1999 | Linder | 604/523 |
| 5,938,589 | A | 8/1999 | Wako et al. | 600/159 |
| 5,938,645 | A | 8/1999 | Gordon | 604/264 |
| 5,941,869 | A | 8/1999 | Patterson et al. | 604/508 |
| 5,947,940 | A | 9/1999 | Beisel | 604/282 |
| 5,989,183 | A | 11/1999 | Reisdorf et al. | |
| 6,001,078 | A | 12/1999 | Reekers | 604/43 |
| 6,007,523 | A | 12/1999 | Mangosong | 604/284 |
| 6,017,339 | A | 1/2000 | Sadamasa | 606/46 |
| 6,086,530 | A | 7/2000 | Mack | |
| 6,110,103 | A | 8/2000 | Donofrio | |
| 6,280,415 | B1 | 8/2001 | Johnson | |
| RE37,772 | E | * | 6/2002 | Kelleher | 600/104 |

\* cited by examiner

FLEXIBLE SLEEVE SLIDINGLY TRANSFORMABLE INTO A LARGE SUCTION SLEEVE

CROSS-REFERENCE TO RELATED APPLICATIONS

This application is a continuation of U.S. patent application Ser. No. 09/579,995, filed May 26, 2000, now U.S. Pat. No. 6,547,724, which in turn, claims priority to and the benefit of U.S. provisional patent application Ser. No. 60/136,007 filed on May 26, 1999, both of which are incorporated herein by reference.

TECHNICAL FIELD

The present invention relates to methods and devices useful for removing unwanted materials such as calculi, deposits and tissues from a body cavity.

BACKGROUND INFORMATION

Currently, urologists performing a procedure known as percutaneous nephrolithotomy (PCNL) often use a rigid nephroscope, a flexible cystoscope, or a flexible ureteroscope in conjunction with flexible baskets or graspers to remove stones and stone fragments from the renal cavity of a patient. A rigid or semi-rigid scope is often used to treat the lower urinary tract, while accessing upper urinary tract needs a flexible scope for negotiating the tortuosity when the ureter crosses the iliac vessels. Because of the high degree of deflexibility required for a scope to travel to the upper urinary tract, in terms of both active and passive deflection, adding accessories to the working channels of a flexible ureteroscope, which compromises the scope's overall deflexibility, is often undesirable. See, *Smith's Textbook of Endourology*, Vol. 1, Ch. 32 (1996, Quality Med. Pub. Inc.).

To remove stones and/or stone fragments, urologists generally use an endoscope coupled with accessories such as baskets or graspers. The use of accessories in the working channels of the endoscope becomes problematic when it comes to treating upper urinary tract because of added constraints on the scope's deflexibility and hence access to the target. Also, using a basket or grasper through a flexible scope can be technically challenging due to the high level of manual dexterity required of an operator to manipulate effectively the basket or grasper to capture and retrieve the stone(s) and/or stone fragment(s). Procedures that use baskets or graspers also are time-consuming since the entire scope must be retracted to remove stone(s) or fragment(s) from the renal cavity. If there are multiple stone(s) or fragment(s) to be removed from a specific area, then every time a flexible scope is retracted, the urologist must maneuver his/her way back to the desired location to get the next stone or fragment. This obviously increases the level of tissue trauma to the patient and the risk of damage to the urinary tract.

Urologists also use lithotripters to crush stones into fragments that are passable through the urinary tract. Lithotripsy devices have been developed which utilize electrohydraulic probes, ultrasonic probes, electromechanical impactors, laser fibers and so on. An example of a lithotripter is a system known as "Lithoclast" that is commercially available from Boston Scientific Corporation of Natick, Mass. Again, the addition of a lithotripter will compromise the scope's deflexibility and thus will limit its use in treating the upper urinary tract. Such limitation also affects the breaking power of a lithotripter and renders treatment of upper urinary tracts longer and less successful.

Suction channels, sometimes with a lithotripter in a parallel working channel, have been integrated into scopes to help remove stones and fragments. For instance, a suction system known as "Lithovac," also available from Boston Scientific Corporation of Natick, Mass., can be matched with the "Lithoclast" lithotripter system to remove stones and/or stone fragments from the renal cavity of a patient during a PCNL procedure. Because an integrated suction channel will further decrease the deflexibility of a flexible scope, the use of lithotripters with integrated suction is limited to renal areas that can be accessed by a rigid device. And even in such cases, the suction channel is often highly limited in its diameter and hence the suction capacity.

SUMMARY OF THE INVENTION

An object of the present invention is thus to provide an effective and efficient means for the removal of stones and other unwanted materials from cavities only accessible by a flexible endoscope, such as the upper urinary tract. A more general objective is to provide a suction means that can remove large targets and be suitable for treatment of all cavities in the body including those accessible by rigid instruments.

The present invention provides devices and related methods for the removal of unwanted materials such as calculi, deposits, tissues (e.g., polyps and tumor cells) and fluid from a patient's (human or animal) body cavity. The invention achieves these objectives by providing a sleeve that is to be placed over an elongated instrument such as a flexible endoscope. The sleeve wall contains a port disposed between the distal opening and proximal opening; the port divides the lumen into a distal lumen and a proximal lumen. When the distal end of the inserted instrument is retracted beyond the port, a seal prevents direct passage of gas or liquid between the sleeve's proximal opening and the port. Hence, a passageway is created between the sleeve's distal opening and the port, and through a portion of the sleeve lumen. When the port is connected to a vacuum source, materials from a treatment site can be removed through the suction passageway. When the port is connected to a source of positive pressure (liquid or gas), it results in irrigation or ventilation of the treatment site through the sleeve's passageway.

Because the passageway so created may have a cross-section as large as the entire cross-section of the sleeve, effective removal of large targets becomes possible. This maximization in the cross-section of the passageway offers a significant advantage over the removal capacity of known suction lumens that are integrated in a rigid, semi-rigid or flexible endoscope. Particularly for treatment of upper urinary tracts where scope deflexibility is crucial, the invention provides the possibility for a flexible scope containing a lithotripter in its working channels to also possess a suction function. The device of the invention also eliminates the need for using flexible forceps and flexible baskets through the working channels of flexible scopes, an operatively difficult and inefficient procedure for treating upper urinary tracts.

The time required to remove stones and their fragments is also substantially reduced with the excellent suction capability of the device of the invention. Because the sleeve remains positioned inside the body cavity, an operator can reinsert the instrument to the earlier position through the guidance of the sleeve. This saves the operator from re-performing the often time-consuming and technically-demanding procedure of maneuvering the medical instrument inside a body cavity such as the tortuous renal cavity. This also saves the patient from further discomfort and tissue trauma.

The sleeve is designed to receive an elongated medical instrument such as a scope and more particularly, a flexible scope such as a flexible cystoscope or a flexible ureteroscope. Therefore, the sleeve can take any shape to accommodate the shape of the instrument, and different segments of the sleeve may assume different shapes. The preferred shape of the sleeve is substantially cylindrical where a cross-section of the sleeve is substantially circular or oval. In a preferred embodiment, the port is connected to a vacuum pump. When the instrument is slid back until its distal end is proximal to the suction port, the space inside the sleeve previously occupied by the instrument becomes a suction passageway. Suction in the distal lumen is made possible by the presence of a seal in the sleeve's proximal lumen. The seal may be in the form of an interference fit between the sleeve member and the instrument (e.g. around its radial surface).

The sleeve can have multiple lumens. Such lumens may be defined by a permanent partition integral with the sleeve, or by temporary structures that may be separated from the sleeve, or it may be created by the insertion of an instrument whose outer diameter is less then the inner diameter of the sleeve. At least one of these lumens may be connected to an aperture and serve as a channel for suction, irrigation or ventilation even when the distal end of the instrument is in the distal lumen. This aperture can be the same port that divides the sleeve lumen into the distal lumen and the proximal lumen. Alternatively, this aperture can be a separate opening.

The sleeve may be used to provide concurrent irrigation to the treatment site. This will prevent collapse of the renal cavity during suction by providing enough fluid flow to the renal cavity to counteract the suction force pulling material and fluid out of the renal cavity. A separate irrigation channel can also be integrated into the sleeve.

In some embodiments of the invention, the sleeve and the instrument are integrated into one unit. In other embodiments of the invention, the sleeve and the instrument are separable and the sleeve becomes disposable after use. This allows it to be manufactured inexpensively and does not require the operator to purchase any additional instrumentation in order to use the sleeve.

The wall forming the sleeve lumen may be made of a rigid, semi-rigid or flexible material. In a preferred embodiment where the sleeve is to enclose a flexible scope used for treating the upper urinary tract, the sleeve is made of flexible materials. As a result, the sleeve will not significantly impact the deflection capabilities of the flexible scope. In addition, the inner and/or outer surface of the sleeve may be coated partially or completely with a lubricious material to further reduce any impact on the deflexibility of the scope, allowing easy positioning and maneuvering around the renal cavity. In another embodiment, on the other hand, there may be structures such as reinforcement materials in the sleeve that prevents the sleeve from ovaling, kinking, or collapsing as a result of bending, manipulation, or suctioning of stone(s) or fragment(s).

The sleeve has a seal that prevents the direct passage of fluid between the port and the proximal opening of the sleeve. An example of the seal is an airtight connection with a portion of the enclosed instrument when the instrument is pulled back beyond the port. When the port is connected to a vacuum source, this seal in that segment of the sleeve allows the formation of a suction passageway from the sleeve's distal opening to the suction port. An example of such a seal is a compressive clamp or an O-ring that tightens around the radial surface of the enclosed instrument. The instrument can also be force-fitted into the sleeve and the force-fitting remains proof when the distal end of the instrument is retracted into the proximal lumen. In that case, the seal comprises a portion of the sleeve's inner surface that is in contact with the instrument. This seal may continue to prevent the direct passage of gas or liquid between the proximal opening and the port even when the distal end of the instrument is distal to the suction port. The seal may comprise a locked position and an unlocked position.

The port is connected to a source of pressurized fluid (gas or liquid), such as a pump. The source may generate negative pressure that causes suction, or it may generate positive pressure to inject fluid (such as saline solution or air). A switch, such as a trumpet valve assembly, may be used to switch the port between the suction mode and the injection mode. The port may be further connected to an on/off switch, and/or a pressure-regulator.

The foregoing and other objects, aspects, features, and advantages of the invention will become more apparent from the following description, figures, and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Reference is now made to the drawings which are presented merely for the purpose of illustrating the general principles of the invention.

Figure 1:
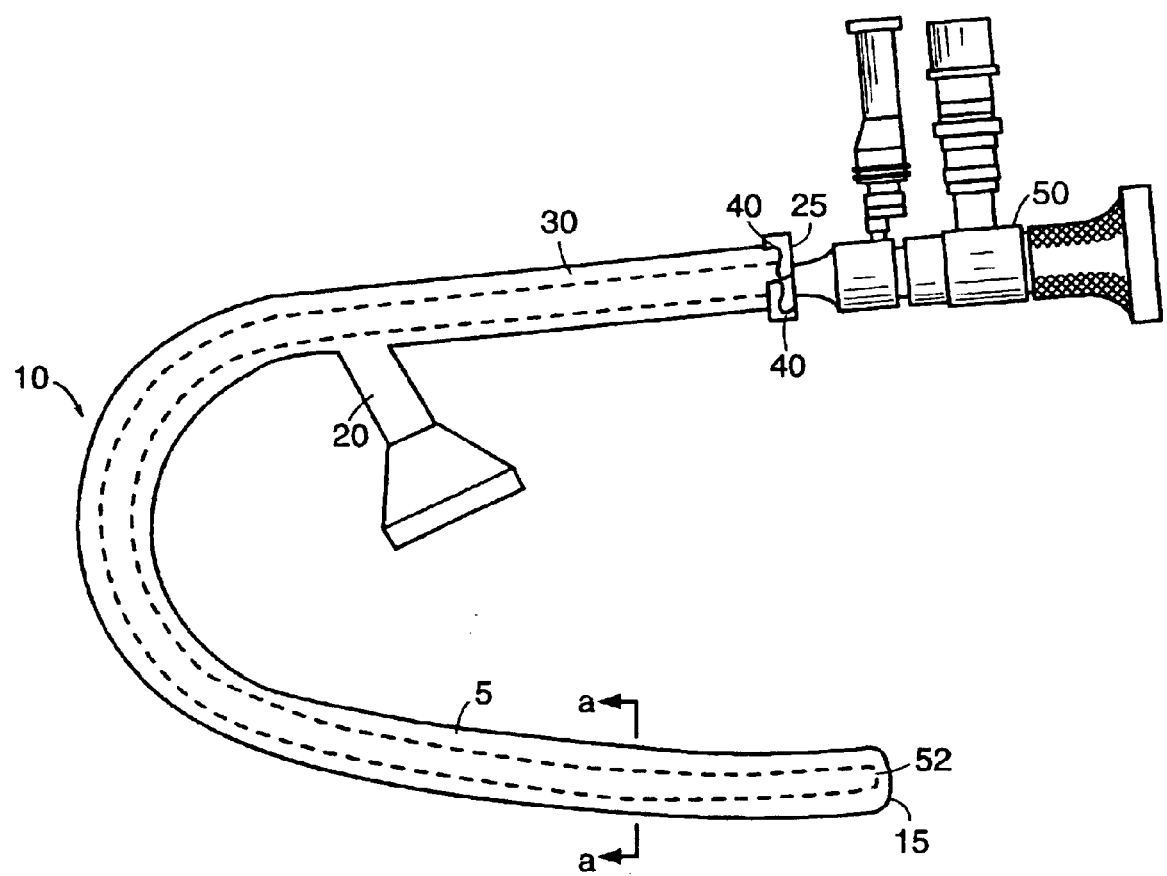
FIG. 1 is a side view of an embodiment of the invention.

Referring to FIG. 1, an embodiment of the sleeve in accordance with the present invention comprises a tubular member 10 that is designed to be placed over an elongated instrument 50, such as a scope as illustrated here. The tubular member 10 has a distal opening 15 and a proximal opening 25 and a third radial opening 20. Opening 20 is a port connected to a source of pressurized fluid (not shown). The port 20 divides the lumen of the sleeve into two segments: the proximal lumen 30 between the proximal opening 25 and the port 20, and the distal lumen 5 between the distal opening 15 and the port 20. The sleeve further comprises a seal 40 that prevents direct passage of gas or liquid between the proximal opening 25 and the port 20. In one mode as illustrated in FIG. 1, the elongated instrument 50 is inserted all the way inside the sleeve and performs its intended functions. In the case of an endoscope, once its distal end 52 is inserted into the distal region of the sleeve, it can be used to carry out diagnostic and therapeutic functions. In this mode, the sleeve 10 is a protective cover or sheath and provides sterility and insulation.

Figure 2:
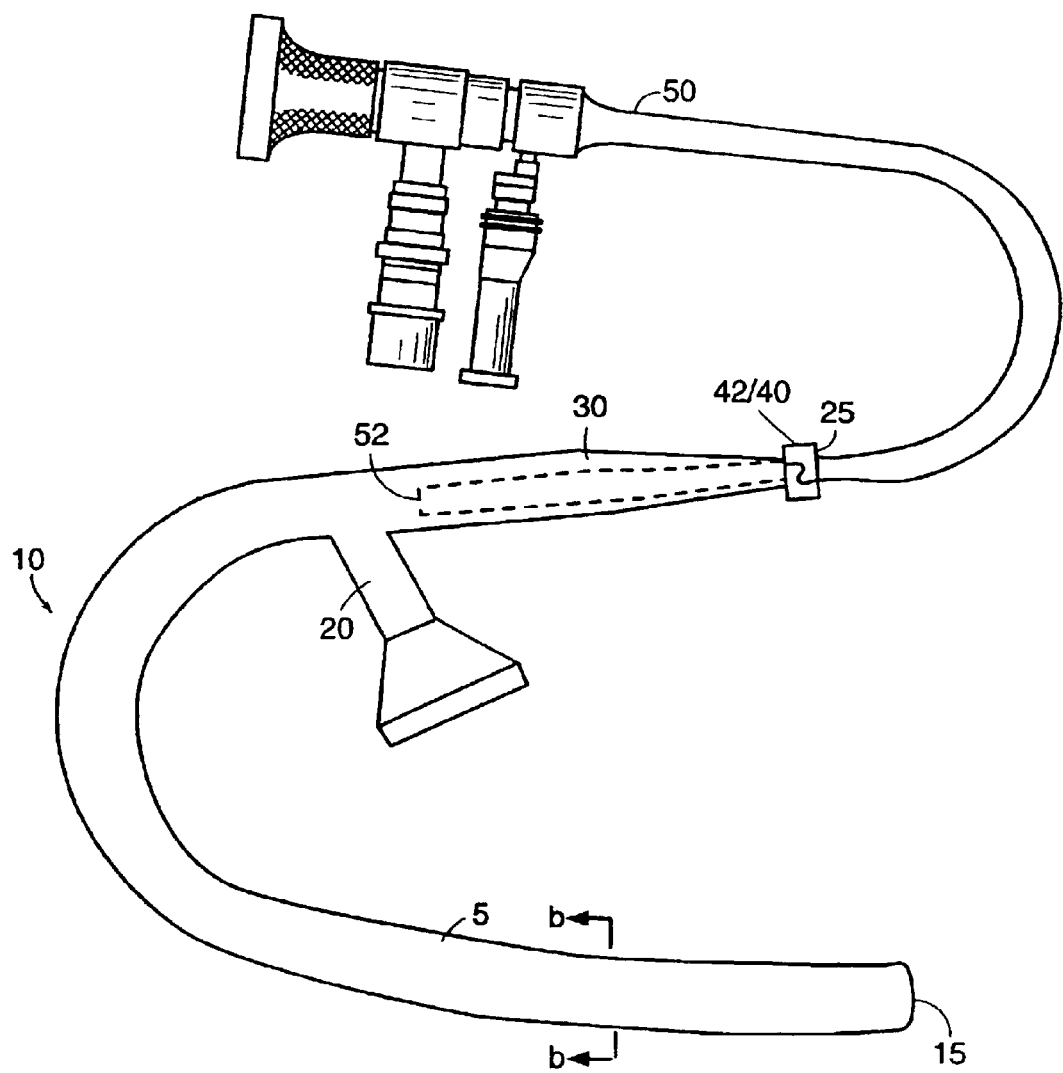
FIG. 2 is a further illustration of the embodiment depicted in FIG. 1.

In FIG. 2, the same embodiment of the invention is shown in a different mode. Here, the inserted instrument 50 is pulled back in the sleeve 10. When the distal end 52 of the instrument 50 is disposed proximal to the port 20, the seal 40 prevents the direct passage of gas or liquid between the proximal opening 25 and the port 20. In this particular illustration, the seal 40 comprises a ring clamp 42 made of elastic steel that locks and exerts a compressive force on a portion of the instrument 50's radial surface. Once the clamp 42 is locked, it provides an interference fit between the proximal end of the sleeve 10 and a portion of the outer, radial surface of the inserted instrument 50. Clamp 42 can also be in the locked position and seal off the proximal end of the sleeve 10 even when instrument 50 is fully inserted in the sleeve such that its distal end 52 is distal to port 20. If this is the case, and if the port 20 is connected to a vacuum source, any space in the sleeve 10 not occupied by instrument 50 will become a suction lumen when the distal end 52 is in the distal lumen 5. In any event, when the instrument is partially retracted such that its distal end 52 is in the proximal lumen 30, the entire distal lumen 5 becomes a passageway for materials to flow between the distal opening 15 and port 20.

A major advantage of the present invention is the maximization in the cross section of the passageway which can be used for suction. The outer diameter of the sleeve 10 can be, in one embodiment, approximately 18 Fr which will allow the device to travel through most infundibula. In one embodiment, the inner diameter of the sleeve is sized to allow suction and removal of stones and fragments up to 5 mm in diameter when the distal end 52 of the scope is in the proximal lumen 30, and up to 2 mm in diameter when the distal end 52 is in the distal lumen 5.

While in the preferred embodiment, the sleeve 10 is detachable from the instrument 50 and hence disposable, it shall be recognized that the invention further contemplates integrating the two into one unit. The sleeve and the instrument may contain structures such as corresponding grooves and protrusions to customarily fit each other and provide effective sealing at least when the distal end 52 of the instrument is in the proximal lumen 30.

The wall forming the sleeve lumen may be made of a rigid, semi-rigid or flexible material. The sleeve can be manufactured through thermoplastic extrusion or injection molding. In a preferred embodiment where the sleeve is to enclose a flexible scope in treating the upper urinary tract, the sleeve is made of a flexible material, preferably of extrudable plastic materials, such as polyurethane, polyethylene, polyethylene teraphthalate, and/or polyvinyl chloride. As a result, the sleeve will not significantly impact the deflection capabilities of the flexible scope, and the scope 50 is able to achieve a deflection of about 120 to 150 degrees with the sleeve 10 over the scope.

In some embodiments of the invention, the sleeve is constructed in such a manner, as recognized by those skilled in the art, to prevent ovaling, kinking, or collapse as a result of bending, manipulation, or suctioning of stones or their fragments. One example is to add reinforcing materials in the form of wires or an intermediate layer in the lumen wall of the sleeve 10. Another example is to insert support rings, inflatable tubes, helical members and other structures such as described in U.S. Pat. No. 6,017,339 to Sadamasa, U.S. Pat. No. 5,569,219 to Hakki et al. and U.S. Pat. No. 5,947,940 to Beisel, all of which are incorporated herein by reference. In a preferred embodiment, the sleeve is passively deflected since it relies on the use of a flexible scope for positioning within the renal cavity, that is, the sleeve is flexible and bends or deflects as an operator controllably bends and deflects the scope.

In one aspect of the invention, the inner and/or outer surface of the sleeve 10 may be coated partially or completely with lubricious materials to allow easy positioning and maneuvering around the renal cavity. Such coating(s) may also help offset any impact on the deflexibility of the flexible scope due to the durometer of the sleeve.

Figure 3A:
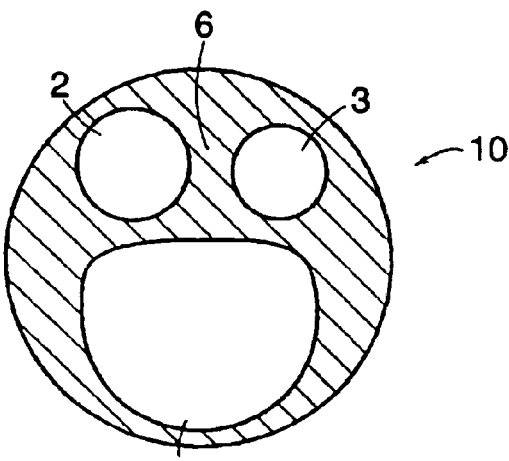
FIGS. 3A–3B are cross-section views, taken along line b—b in FIG. 2, showing the lumens of various embodiments of the sleeve.

In another aspect of the invention, the sleeve may contain multiple lumens defined by partition structures. Apertures connected to these lumens may be part of the sleeve's distal opening, proximal opening, or its radial surface. As shown in FIG. 3A, the sleeve 10 may contain, for example, three lumens defined by partition structure 6. Lumen 1 is sized for insertion of the medical instrument (not shown). One of the lumens can be used as an irrigation or ventilation channel 3 connected to a source of pressurized fluid. Lumen 2 illustrates another working channel.

Figure 3B:
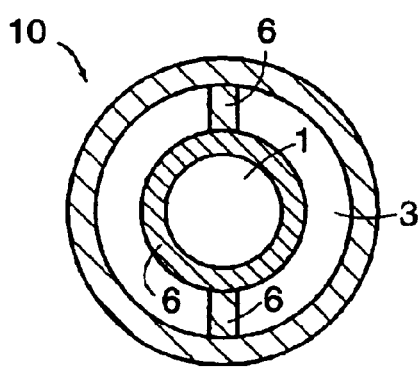

The lumens can be substantially co-axial, as shown in FIG. 3B. All or one of the outer lumens may be used as the irrigation/ventilation channel 3 connected through an aperture (not shown) to a source of irrigation or ventilation. That aperture may be the port 20. The channel 3 can run along the length of the sleeve 10, which prevents the collapse of the cavity under treatment during suction by providing enough fluid flow to the cavity to counteract the vacuum caused by suction.

Figure 3C:
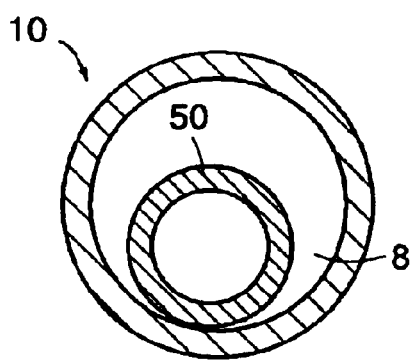
FIG. 3C is a cross-section view, taken along line a—a in FIG. 1, showing the lumen of an embodiment of the sleeve with an instrument inside.

Referring to FIG. 3C, when the outer diameter of the instrument 50 is less than the inner diameter of the sleeve 10, a lumen 8 is created by virtue of space in the sleeve unoccupied by the instrument. Lumen 8 can be connected, through an aperture in the sleeve's proximal end or in the sleeve's radial surface, to a source of pressurized fluid and be used as an irrigation or ventilation channel. Lumen 8 may also be connected to the port 20, and serve as a suction passageway when the distal end of the instrument 50 is in the distal lumen and the port 20 is connected to a vacuum source. A continuous low-pressure flow may be supplied through lumen 8 to remove stones or fragments while the instrument 50 operates. Furthermore, since the port 20 may be further connected to a source of positive pressure and be used to inject fluids or gases to the treatment site (described below), lumen 8 may be used as an irrigation or ventilation channel in that manner.

Figure 4A:
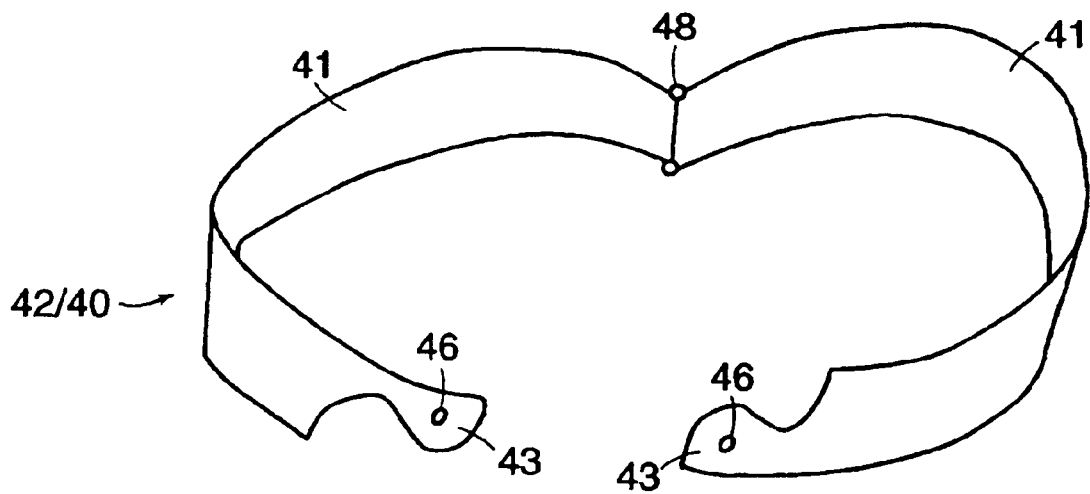
FIG. 4A is a prospective view of an embodiment of the seal in accordance with the invention.

In one aspect, the seal 40 can assume many different structures and configurations. As depicted in FIGS. 1 and 2, and in more detail in FIG. 4A, the seal 40 can be a compressive clamp 42 or an O-ring made of steel. Referring to FIG. 4A, an embodiment of the clamp 42 in accordance with the invention is in the shape of a bracelet that is to be placed over the proximal portion of the sleeve (not shown). The clamp 42 may include two arms 41, connected by a hinge 48. The two arms 41 lock through two tooth-like structures 43, which are complementary in shape and will lock when an operator squeezes them together and past each other. There are small knob-like protrusions 46 fixed on structures 43. The operator can unlock structures 43 by pushing the two knobs 46 outward simultaneously. There can be additional structures attached inside the arms 41 where contact with the sleeve is made. An example of such additional structures is a pad made of materials such as plastics, rubber, leather or sponge. When the operator locks the clamp 42 around the proximal portion of the sleeve, the clamp 42 tightens the sleeve and provides an interference fit between the sleeve and the medical instrument inside. The option of having other structures between the sleeve and the instrument is not contemplated as negating the existence of an interference fit. Other devices known to one skilled in the mechanical art that can be used to seal off the sleeve's proximal opening against the enclosed instrument, such as rubber bands and devices described in U.S. Pat. No. 5,775,325 to Russo, incorporated herein by reference, are also contemplated by the present invention.

Figure 4B:
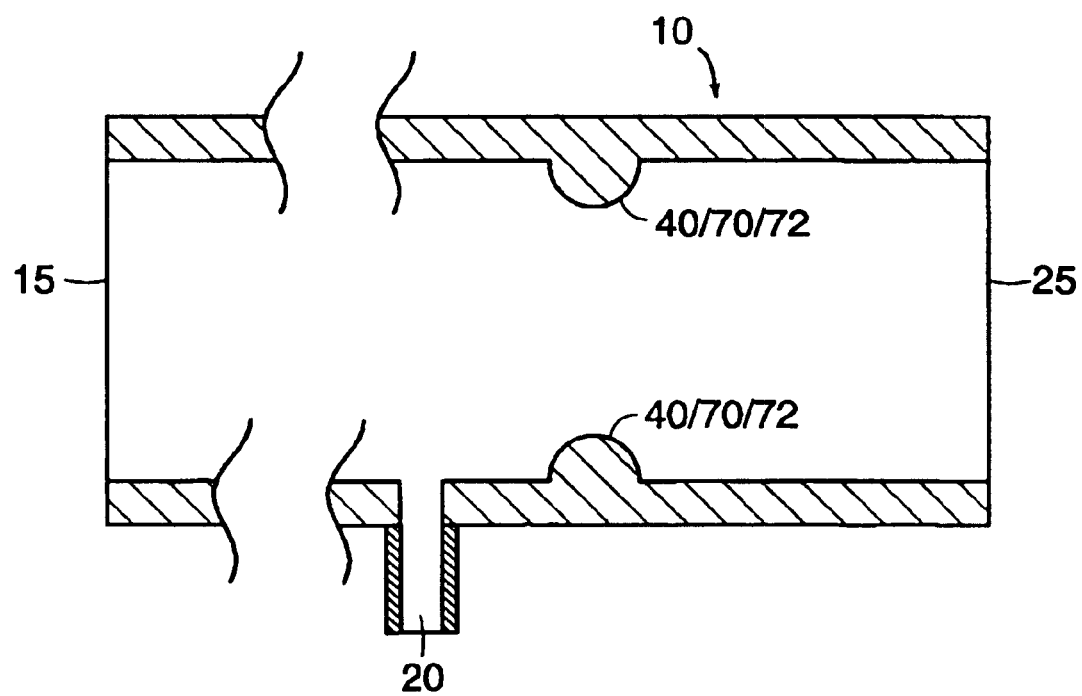
FIG. 4B is a schematic view of another embodiment of the seal in accordance with the invention.

Referring to FIG. 4B, in another embodiment, the seal 40 can comprise a portion of the inner surface of the sleeve itself that protrudes inward as a constrictor 70. This ring of protrusion 72 between the proximal opening 25 and the port 20 can be made of the same material and be integral to the sleeve or of a different material that has a higher or lower durometer. The size of constrictor 70 is designed to provide an interference fit between the sleeve's inner surface and the inserted instrument. Alternatively, the constricting ring may be disposed on the outer surface of the sleeve and exert inward radial forces on the sleeve that compress the inner surface tightly against the surface of the instrument. The constricting ring may reside in a groove carved on the outer surface of the sleeve.

If the inner diameter of the sleeve and the outer diameter of the instrument are substantially the same and therefore the instrument is force-fitted into the sleeve, then the seal 40 comprises portions of the sleeve's inner surface and the instrument's outer radial surface that are in contact with each other.

Referring back to FIGS. 3A and 3B, in certain embodiments, such as those depicted here, where there are lumens other than lumen 1, which is for insertion of the instrument 50, the seal 40 (not shown) may or may not seal off those lumens. Therefore, the irrigation or ventilation channel 3, for example, may continue to transport fluids to the treatment site, when the seal 40 seals off the proximal end of lumen 1. The route where fluids travel from the sleeve's proximal opening, through an irrigation or ventilation channel, to the sleeve's distal opening and then to the port 20 is not contemplated as a "direct" passage of fluids between the proximal opening and the port.

The port 20 is connected to a source of pressurized fluid, such as a pump. In one aspect of the invention, the source may generate either negative pressure to cause suction or positive pressure to inject fluid or air to the site of treatment. Alternatively, the source of positive pressure (e.g., for irrigation or ventilation) may be separate from the source of negative pressure (e.g., a vacuum pump) and the port may be linked to both. In that case, the port may be further connected to a device allowing the operator to switch from one connection to the other. An example of such a device is a trumpet valve assembly, described in U.S. Pat. No. 5,449,145 to Wortrich, incorporated herein by reference. A source of pressurized gas or liquid such as a gravity-based drip-irrigation system is contemplated by the present invention as a source of positive pressure. In any event, the seal 40 prevents direct passage of gas or liquid between the port and the sleeve's proximal opening.

Whether the suction port is linked to a source of positive pressure, negative pressure or both, the suction port may be further connected to a switch or valve that turns the pressure on and off (e.g. a trumpet valve), and/or a pressure-regulator. Examples of such control devices are described in publications such as U.S. Pat. No. 5,882,348 to Winterton et al., U.S. Pat. No. 5,938,589 to Wako et al., and U.S. Pat. No. 5,730,727 to Russo, all incorporated herein by reference.

A further aspect of the invention addresses the risk of scope damage from stones and their fragments hitting the lens at the distal end of the scope inserted in the sleeve. A separate soft bumper, mesh, or other like barrier structure can be attached to the distal end of the scope for lens protection. A stream of irrigating fluid will also cushion the scope against the impact of stones and their fragments. The irrigation will also help clean the lens for better viewing.

Different embodiments and various features of the invention can be combined in the same device in accordance with the invention. Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A medical device sleeve, comprising:
    a flexible tubular member defining a distal opening at a distal end, a proximal opening at a proximal end, and a lumen extending from the distal opening to the proximal opening, the tubular member further comprising a port that enters the lumen at a location between the distal opening and the proximal opening, the port dividing the lumen into a distal portion and a proximal portion, the port also for connection to a vacuum source; and
    a clamp disposed along the flexible tubular member between the port and the proximal opening, configured to allow an elongated instrument to be extended and retracted in the lumen when the clamp is unlocked, and to provide a seal between the tubular member and the instrument when the clamp is locked and the instrument is retracted into the proximal portion of the lumen, such that suction may be applied, via the port, in a space comprising at least a portion of the distal portion of the lumen.

2. The sleeve of claim 1, wherein the clamp comprises a ring.

3. The sleeve of claim 1, wherein the clamp is made of elastic steel.

4. The sleeve of claim 1, wherein the distal portion of the lumen has a diameter of at least 5 mm.

5. The sleeve of claim 4 wherein the distal portion of the lumen has a diameter of at least 6 mm.

6. The sleeve of claim 1, wherein suction is applied in the entire distal portion of the lumen when the clamp is locked to provided the seal.

7. The sleeve of claim 1, wherein the port is also for connection to a source of positive pressure.

8. The sleeve of claim 7, wherein the port is further for connection to a selector for selecting between the vacuum source and the source of positive pressure.

9. The sleeve of claim 1, wherein the port is further for connection to a pressure regulator.

10. The sleeve of claim 1, wherein the port is further for connection to an on/off switch.

11. The sleeve of claim 10, wherein the switch comprises a trumpet valve.

12. The sleeve of claim 1, further comprising a partition in the tubular member dividing the lumen into multiple smaller lumens.

13. The sleeve of 12 wherein at least one of the multiple smaller lumens is for connection to a source of pressurized fluid.

14. The sleeve of claim 1, wherein the tubular member comprises a flexible material.

15. The sleeve of claim 1, wherein the tubular member comprises a reinforcing material.

16. The sleeve of claim 1, wherein at least a portion of the tubular member is coated with a lubricant.

17. The sleeve of claim 1, wherein the sleeve is disposable.

18. A medical device comprising:
   an endoscope;
   a flexible sleeve placed over at least a portion of the endoscope, the sleeve defining a distal opening at a distal end, a proximal opening at a proximal end, and a lumen extending from the distal opening to the proximal opening, the sleeve further comprising a port that enters the lumen at a location between the distal opening and the proximal opening, the port dividing the lumen into a distal portion and a proximal portion, the port also for connection to a vacuum source; and
   a clamp disposed along the sleeve between the port and the proximal opening, configured to allow the endoscope to be extended and retracted in the lumen of the sleeve when the clamp is unlocked, and to provide a seal between the sleeve and the endoscope when the clamp is locked and the endoscope is retracted into the proximal portion of the lumen, such that suction may be applied, via the port, in a space comprising at least a portion of the distal portion of the lumen.

19. The medical device of claim 18 wherein the endoscope comprises a ureteroscope.

20. The medical device of claim 18 comprising a lithotripter.

21. A medical device, comprising:
   a flexible tubular member defining a distal opening at a distal end, a proximal opening at a proximal end, and a lumen extending from the distal opening to the proximal opening, the lumen being configured to allow an elongated instrument to be extended and retracted in the lumen, the tubular member further comprising a port for connection to a vacuum source and that enters the lumen at a location between the distal opening and the proximal opening to divide the lumen into a distal portion and a proximal portion; and
   seal means for providing a seal between the elongated instrument and the flexible tubular member when the elongated instrument is located in the lumen such that suction may be applied, via the port, in a space comprising at least a portion of the distal portion of the lumen to retrieve objects through the lumen, the seal means being located along the flexible tubular member between the port and the proximal opening.

22. The sleeve of claim 21, wherein the distal portion of the lumen has a diameter of at least 5 mm.

23. The sleeve of claim 21, wherein the distal portion of the lumen has a diameter of at least 6 mm.

24. A medical device, comprising:
   a flexible tubular member defining a distal opening at a distal end, a proximal opening at a proximal end, and a lumen extending from the distal opening to the proximal opening, the lumen being configured to allow an elongated instrument to be extended and retracted in the lumen, the tubular member further comprising a port for connection to a vacuum source and that enters the lumen at a location between the distal opening and the proximal opening to divide the lumen into a distal portion and a proximal portion; and
   a seal device that defines a seal between the elongated instrument and the flexible tubular member when the elongated instrument is located in the lumen such that suction may be applied, via the port, in a space comprising at least a portion of the distal portion of the lumen to retrieve objects through the lumen, the seal device being located along the flexible tubular member between the port and the proximal opening.

25. The medical device of claim 24, wherein the tubular member includes another lumen.

26. The medical device of claim 24, wherein at least a portion of the tubular member is coated with a lubricant.

27. The medical device of claim 24, wherein the medical device is disposable.

28. The medical device of claim 24, wherein the seal device includes a clamp that locks and unlocks.

29. A medical device, comprising:
   an endoscope;
   a flexible tubular member defining a distal opening at a distal end, a proximal opening at a proximal end, and a lumen extending from the distal opening to the proximal opening, the lumen being configured to allow the endoscope to be extended and retracted in the lumen, the tubular member further comprising a port for applying suction to the lumen at a location between the distal opening and the proximal opening and that divides the lumen into a distal portion and a proximal portion; and
   a seal device that defines a seal between the endoscope and the flexible tubular member when the endoscope is located in the lumen such that suction may be applied, via the port, in a space comprising at least a portion of the distal portion of the lumen to retrieve objects through the lumen.

* * * * *

UNITED STATES PATENT AND TRADEMARK OFFICE
CERTIFICATE OF CORRECTION

PATENT NO. : 6,997,867 B2  Page 1 of 1
APPLICATION NO. : 10/389306
DATED : February 14, 2006
INVENTOR(S) : Jon Soble et al.

It is certified that error appears in the above-identified patent and that said Letters Patent is hereby corrected as shown below:

Column 8,
Line 53, replace "provided" with --provide--

Column 9,
Line 34, insert --further-- after "claim 18"

Column 10,
Line 3, replace "sleeve" with --medical device--

Column 10,
Line 5, replace "sleeve" with --medical device--

Signed and Sealed this

Twentieth Day of March, 2007

JON W. DUDAS
*Director of the United States Patent and Trademark Office*